US009675512B2

(12) United States Patent
Kare et al.

(10) Patent No.: US 9,675,512 B2
(45) Date of Patent: Jun. 13, 2017

(54) LEG LOCOMOTION DEVICES

(71) Applicant: Elwha LLC, Bellevue, WA (US)

(72) Inventors: Jordin T. Kare, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 808 days.

(21) Appl. No.: 13/830,448

(22) Filed: Mar. 14, 2013

(65) Prior Publication Data

US 2014/0276262 A1 Sep. 18, 2014

(51) Int. Cl.

*A61F 2/48* (2006.01)
*A61H 1/02* (2006.01)
*A61H 3/00* (2006.01)

(52) U.S. Cl.

CPC .......... *A61H 1/024* (2013.01); *A61H 1/0244* (2013.01); *A61H 1/0266* (2013.01); *A61H 3/00* (2013.01);

(Continued)

(58) Field of Classification Search

CPC .......... A61H 1/00; A61H 1/02; A61H 1/0237; A61H 1/024; A61H 1/0244; A61H 1/0262; A61H 3/00; A61H 2003/007; A61H 2201/00; A61H 2201/0157; A61H 2201/12; A61H 2201/1207; A61H 2201/1215; A61H 2201/123; A61H 2201/14; A61H 2201/16; A61H 2201/165; A61H 2201/1652; A61H 2201/50; A61H 2201/5007; A61H 2201/5061; A61H 2201/5064; A61H 2203/00; A61H 2203/04; A61H 2203/0406; A61H 2205/00; A61H 2205/10; A61H 2205/106; A61H 2205/108

See application file for complete search history.

(56) References Cited

U.S. PATENT DOCUMENTS 406,328 A 7/1889 Yagn
420,178 A 1/1890 Yagn (Continued)

FOREIGN PATENT DOCUMENTS

WO WO 99/05991 2/1999

OTHER PUBLICATIONS

PCT International Search Report; International App. No. PCT/US2014/023453; Jul. 1, 2014; pp. 1-4.

(Continued)

*Primary Examiner* — Steven Douglas
(74) *Attorney, Agent, or Firm* — Foley & Lardner LLP

(57) ABSTRACT

A leg locomotion device includes a frame having a leg coupler configured to mount the frame to a user's leg, the frame also includes two frame components movable relative to one another in response to movement of the user's leg, an energy harvesting device coupled to the frame and configured to harvest energy from the movement of the two frame components during a first portion of a stride, an energy storage device coupled to the energy harvesting device, the energy storage device configured to store harvested energy over more than one stride, and an assist device coupled to the frame, coupled to the energy storage device to receive energy therefrom, and configured to move the frame components relative to one another to selectively assist with movement of the user's leg during a second portion of the stride.

34 Claims, 4 Drawing Sheets

(52) U.S. Cl.
CPC ................ *A61H 2201/0173* (2013.01); *A61H 2201/1246* (2013.01); *A61H 2201/501* (2013.01); *A61H 2201/5058* (2013.01); *A61H 2201/5071* (2013.01); *A61H 2201/5079* (2013.01); *A61H 2201/5082* (2013.01); *A61H 2201/5092* (2013.01); *A61H 2201/5097* (2013.01); *A61H 2230/045* (2013.01); *A61H 2230/065* (2013.01); *A61H 2230/208* (2013.01); *A61H 2230/305* (2013.01); *A61H 2230/425* (2013.01); *A61H 2230/505* (2013.01); *A61H 2230/605* (2013.01); *A61H 2230/855* (2013.01)

(56) References Cited

U.S. PATENT DOCUMENTS

| | | | | |
|---|---|---|---|---|
| 420,179 | A | 1/1890 | Yagn | |
| 438,830 | A | 10/1890 | Yahn | |
| 4,408,600 | A | 10/1983 | Davis | |
| 4,936,030 | A | 6/1990 | Rennex | |
| 4,967,734 | A | 11/1990 | Rennex | |
| 5,011,136 | A | 4/1991 | Rennex | |
| 5,362,288 | A | 11/1994 | Razon | |
| 5,476,441 | A * | 12/1995 | Durfee | A61N 1/36003 434/112 |
| 6,500,138 | B1 | 12/2002 | Irby et al. | |
| 6,834,752 | B2 | 12/2004 | Irby et al. | |
| 7,393,335 | B2 | 7/2008 | Carvey et al. | |
| 7,549,969 | B2 | 6/2009 | Van Den Bogert | |
| 8,057,410 | B2 * | 11/2011 | Angold | A61H 3/00 601/35 |
| 2002/0094919 | A1 | 7/2002 | Rennex et al. | |
| 2003/0062241 | A1 | 4/2003 | Irby et al. | |
| 2004/0040180 | A1 | 3/2004 | Rennex et al. | |
| 2004/0049291 | A1 | 3/2004 | Deharde et al. | |
| 2005/0059908 | A1 * | 3/2005 | Bogert | A61F 5/0102 601/5 |
| 2005/0262272 | A1 | 11/2005 | Christensen | |
| 2006/0046909 | A1 | 3/2006 | Rastegar et al. | |
| 2006/0249315 | A1 | 11/2006 | Herr et al. | |
| 2010/0160121 | A1 | 6/2010 | Rastegar et al. | |
| 2010/0198124 | A1 * | 8/2010 | Bhugra | A61B 5/0205 602/5 |
| 2012/0259431 | A1 * | 10/2012 | Han | A61F 5/0125 623/24 |
| 2013/0056981 | A1 * | 3/2013 | Mullins | F03G 5/06 290/7 |
| 2015/0025423 | A1 * | 1/2015 | Caires | A61H 1/024 601/35 |

OTHER PUBLICATIONS

Beard, Jonathan, "DARPA's Bio-Revolution An Array of Programs Aims to Improve the Safety, Health, and Well-being of the Military and Civilians Alike" 50 Years of Bridging the Gab, Apr. 2008, 7 pages.

Bramble et al., "Endurance running and the evolution of Homo", Nature, vol. 432, Nov. 18, 2004, pp. 345-352.

Marks, Paul, "Fake foot with smarts boosts walking efficiency", New Scientist, Feb. 17, 2010, 2 pages.

Minetti et al., "Energy cost of walking and running at extreme uphill and downhill slopes", Journal of Applied Physiology, vol. 93, Sep. 2002, pp. 1039-1046.

Phillips, Kathryn, "Bionic Ankles cut walking costs", The Journal of Experimental Biology, 2008, 1 page.

Rubenson et al., Adaptations for economical bipedal running: the effect of limb structure on three-dimensional joint mechanics, Journal of the Royal Society, 2010, 16 pages.

Sorge, Erik, "Navy SEALs Could Turn Superhuman with Pentagon's PowerSwim", Popular Mechanics, Oct. 1, 2009, 3 pages.

* cited by examiner

LEG LOCOMOTION DEVICES

BACKGROUND

The present invention relates generally to the field of locomotion devices for human legs.

SUMMARY

One embodiment of the invention relates to a leg locomotion device including a frame having a leg coupler configured to mount the frame to a user's leg, the frame also includes two frame components movable with respect to one another in response to movement of the user's leg, an energy harvesting device coupled to the frame and configured to harvest energy from the movement of the two frame components during a first portion of a stride, an energy storage device coupled to the energy harvesting device, the energy storage device configured to store harvested energy over more than one stride of the user's leg, and an assist device coupled to the frame, coupled to the energy storage device to receive energy therefrom, and configured to move the frame components relative to one another to selectively assist with movement of the user's leg during a second portion of the stride.

Another embodiment of the invention relates to a leg locomotion system including a first leg locomotion device, a second leg locomotion device, and an energy storage device. The first leg locomotion devices includes a first frame configured to be mounted to a user's leg proximate a first leg joint, the first frame including two first frame components movable relative to one another in response to movement of the user's leg at the first leg joint, a first energy harvesting device coupled to the first frame and configured to harvest energy from the movement of the two first frame components during a first portion of a stride of the user's leg, and a first assist device coupled to the first frame and configured to move the first frame components relative to one another to selectively assist with movement of the user's leg at the first leg joint during a second portion of the stride. The second leg locomotion device includes a second frame configured to be mounted to the user's leg proximate a second leg joint, the second frame including two second frame components movable relative to one another in response to movement of the user's leg at the second leg joint, a second energy harvesting device coupled to the second frame and configured to harvest energy from the movement of the two second frame components during the first portion of the stride, and a second assist device coupled to the second frame and configured to move the second frame components relative to one another to selectively assist with movement of the user's leg at the second leg joint during the second portion of the stride. The energy storage device is coupled to the first and second energy harvesting devices, configured to store harvested energy from the first and second energy harvesting devices over more than one stride of the user's leg, and coupled to the first and second assist devices to provide energy thereto.

Another embodiment of the invention relates to a method of operating a leg locomotion device including the steps of mounting a frame to a user's leg, the frame including two frame components movable relative to one another, moving the two frame components in response to movement of the user's leg, harvesting energy from the movement of the two frame components during a first portion of a stride of the user's leg with an energy harvesting device, storing harvested energy in an energy storage device over more than one stride of the user's leg, providing energy from the energy storage device to an assist device, and activating the assist device to move the two frame components relative to one another to assist with movement of the user's leg during a second portion of the stride of the user's leg.

Another embodiment of the invention relates to a leg braking device including a frame having a leg coupler configured to mount the frame to a user's leg and an energy absorbing device coupled to the frame and configured to absorb a downhill load associated with a change in elevation from foot-off to foot-strike of a downhill stride of the user's leg.

Another embodiment of the invention relates to a method of braking during downhill striding including the steps of mounting a frame to a user's leg and absorbing a downhill load associated with a change in elevation from foot-off to foot-strike of a downhill stride of the user's leg with an energy absorbing device coupled to the frame.

Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

Figure 1:
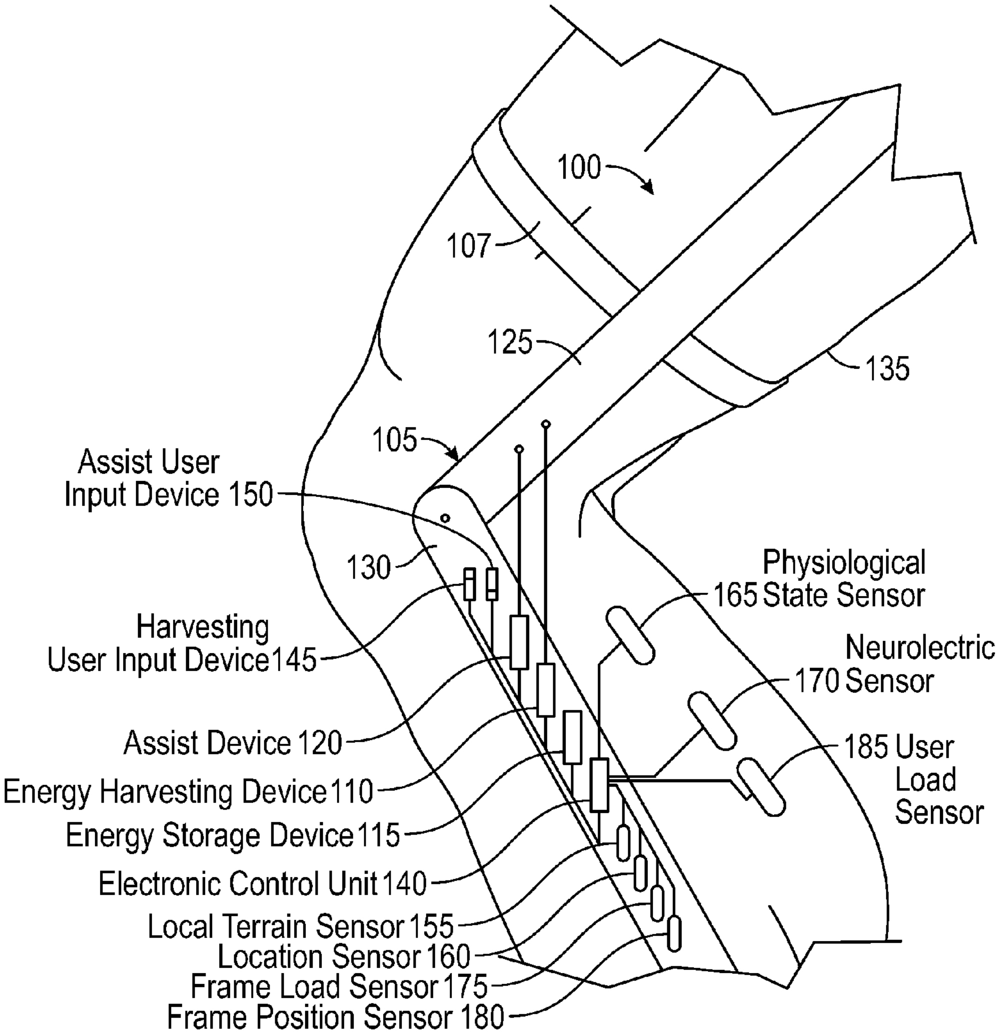
FIG. 1 is a schematic diagram of a leg locomotion device according to an exemplary embodiment.

The skilled artisan will understand that the drawings primarily are for illustrative purposes and are not intended to limit the scope of the inventive subject matter described herein.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Human self-propelled location by striding (i.e., walking, running, and all other forms of striding) is less energy efficient than other forms of man-powered location (e.g., cycling, skating). For example, walking requires about 330 kJ/km while cycling requires only about 120 kJ/km. Because striding is the most prevalent form of human locomotion, any improvements in the energy efficiency of striding are potentially valuable.

A stride of a person's leg is measured from initial foot-strike when foot hits ground (i.e., the surface upon which person is striding) through foot-off when foot leaves ground to subsequent foot-strike when foot hits ground again.

A portion of the energy expended during a stride is actually used to propel the person over the ground, but when walking or running on level ground, some energy is expended non-propulsively, for example in accelerating the leg forward after foot-off and then decelerating it before foot-strike. Various schemes have been proposed to reduce this non-propulsive expenditure, typically by capturing and storing some kinetic energy of body or limb motion and returning it at another point within one stride. However, the benefit of these schemes is generally small in normal walking, and they provide no significant assistance in climbing or descending, or moving over rough terrain.

It is known to capture energy from walking or running and use it to generate electricity, for example for recharging personal electronic devices. However, such generators are seldom efficient, and do not provide any assistance in walking; nor do they respond to the walker's pace, effort level, terrain, etc.

It is known to provide assistance in walking or running using power from an external source, such as a battery or motor, through the use of an external frame or "exoskeleton"; the requirement for an external power source has made such devices impractical for most uses.

Accordingly, there is a need for a leg locomotion device which efficiently captures energy from walking or running when a person is willing and able to provide it, such as when walking on level ground, and which can efficiently return the energy when most needed, for example when running, climbing or descending a slope, climbing stairs, etc.

Such a leg locomotion device would be of particular interest to persons carrying loads by foot and/or travelling by foot for long distances or for long periods of time. For example, such a leg locomotion device would be of particular interest to persons required to carry heavy loads over distance (e.g., soldiers, firefighters, etc.), persons who carry heavy loads over distance by choice (e.g. hikers, outdoorsmen, etc.), and persons who carry lighter loads or are on their feet for long periods of time (e.g., lawn maintenance workers, police officers, postal carriers, deliverymen, etc.).

Such a leg locomotion device may also provide additional functions relating to locomotion, including intra-stride energy transfer for increased walking efficiency, generation of electric power for external use, or assistance in walking using external power.

Referring to FIG. 1, a leg locomotion device 100 according to an exemplary embodiment is illustrated. Leg locomotion device 100 includes frame 105, energy harvesting device 110, energy storage device 115, and assist device 120.

Figure 2:
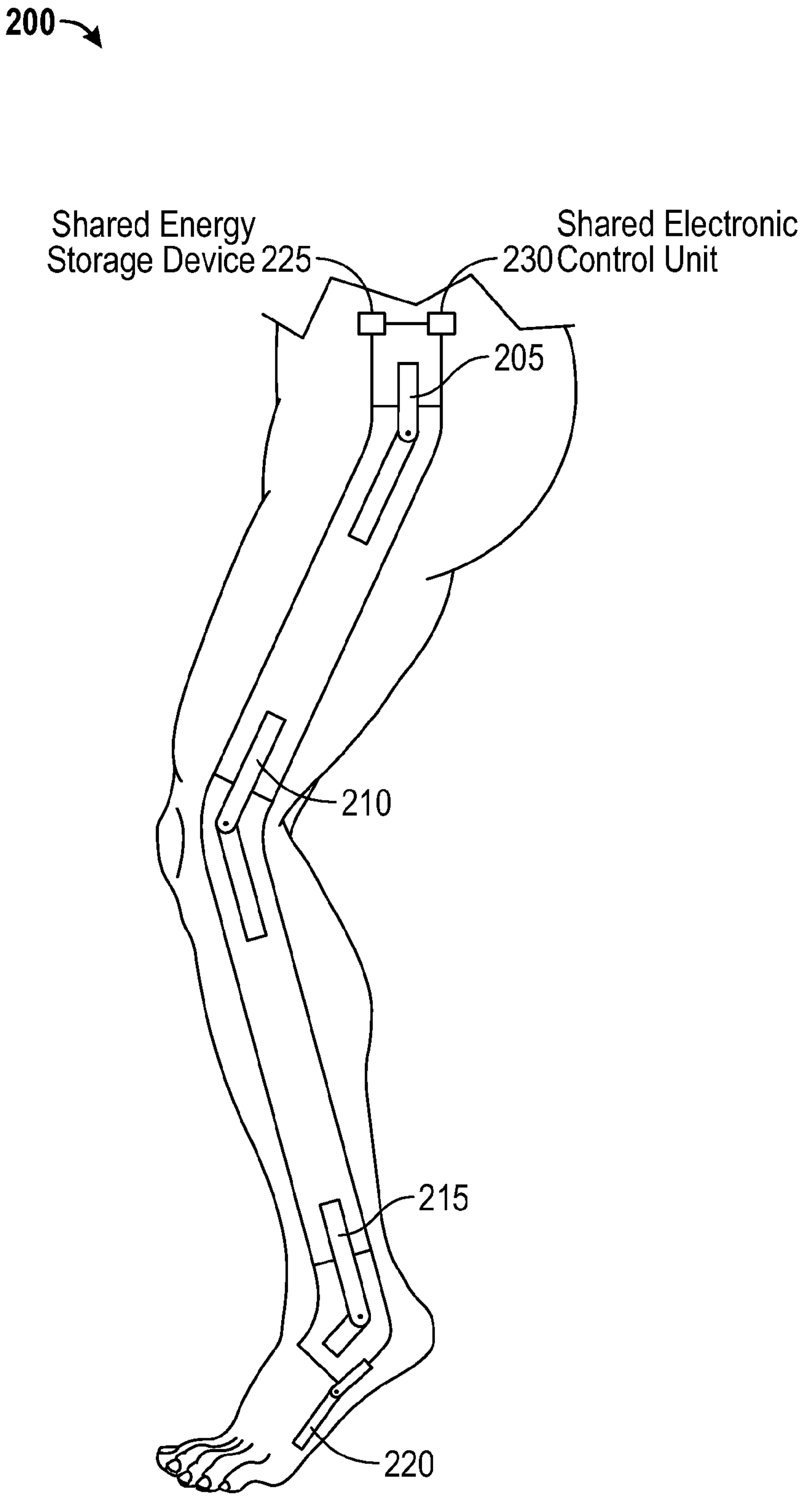
FIG. 2 is a schematic diagram of a leg locomotion system according to an exemplary embodiment.

Frame 105 includes two frame components 125 and 130 and mounts to a user's leg 135. The frame 105 can be mounted to the user's leg by an appropriate leg coupler 107 (e.g., strap, a compression mount, wrap, adhesive, buckle, etc.). Frame components 125 and 130 are movable with respect to one another in response to movement of user's leg 135. Frame 105 is mounted proximate a joint of user's leg 135. For the purposes of this application, user's "leg" includes user's hip and foot and extends from hip to foot. As shown in FIG. 1, frame 105 is mounted across user's knee so that frame component 125 is secured to user's upper leg and frame component 130 is secured to user's lower leg so that frame components 125 and 130 move (e.g., pivot, rotate) with respect to one another as user moves his knee. Frame 105 can be mounted proximate other joints of user's leg 135. For example, as shown in FIG. 2, frame 105 can be mounted at the user's hip, ankle, or arch of the foot. In some embodiments, frame 105 is rigid and lightweight. For example, frame 105 can be made entirely or in part from aluminum, carbon fiber, and other lightweight materials.

Energy harvesting device 110 is coupled to frame 105. Energy harvesting device 110 is coupled to both frame components 125 and 130 to harvest energy from movement of frame components 125 and 130 relative to one another. Energy harvesting device 110 harvests energy by converting the kinetic energy of the movement of frame components 125 and 130 due to the movement of user's leg 135 into storable energy (e.g., electric, hydraulic, pneumatic, etc.). Energy harvesting device 110 harvests energy during a portion of a stride of user's leg 135. In some embodiments, energy harvesting device 110 harvests energy between foot-off and subsequent foot-strike. In some embodiments, energy harvesting device 110 harvests energy between foot-off and the change in direction of user's foot from backwards to forwards, thereby harvesting the energy used for decelerating user's leg during a normal stride. Examples of energy harvesting device 110 include a generator for converting mechanical energy to electrical energy, a pump or piston for pressurizing a hydraulic fluid, and a compressor or piston for compressing air.

The operation of the energy harvesting device 110 will be experienced by the user as a force acting to oppose some part of the motion of the user's leg. The strength of this force, and the corresponding rate at which energy is harvested, may vary during the portion of the stride in which energy is harvested; the profile of force vs. time or force vs. leg position may be selected, for example, to maximize the efficiency of energy collection, or to minimize the effect of the energy harvesting on the user's natural stride. The variation in the force may be set at least in part by the design of the frame and energy harvesting device, for example by incorporating cams or linkages which provide varying mechanical leverage depending on the position of the user's leg, or may be controllable, for example by varying the load on an electrical generator.

Both the instantaneous rate of energy harvesting and the total energy harvested within a portion of a stride may be either selectable or continuously variable over some range. For example, energy harvesting device 110 may be configured to apply a level between 0% and 100% of a maximum amount of force to the user's leg uniformly over an entire portion of a stride, or to always (when activated) apply 50% of a maximum amount of force for the first half of the portion, and a selectable amount of force during the second half. The maximum amount of force may be determined by the frame and/or energy harvesting device (i.e., the strength of the frame members, or the power rating of a generator), or by the capabilities of the user (i.e., the system may be adjusted so that the user is just able to walk comfortably on level ground when the energy harvesting device 110 is set to its maximum level). In some embodiments, energy harvesting device 110 harvests during a useful portion of a stride (e.g., foot-strike to foot-off) in order to harvest energy during easy or normal user exertion (e.g., traversing flat terrain) in order to use that energy later during more difficult user exertion (e.g., traversing uphill or rough terrain).

Energy storage device 115 is coupled to energy harvesting device 110 to store harvested energy. As shown in FIG. 1, energy storage device 115 is coupled to frame component 130. In other embodiments, energy storage device 115 is coupled elsewhere on frame 105 or coupled to user at other locations. Energy storage device 115 stores harvested energy over more than one stride of the user's leg. In this way, user can choose when to make use of the stored harvested energy on an on-demand basis. This differs from energy storage devices that store and return energy to the user within the length of a single stride (e.g., a spring that is compressed between foot-off and the change in direction of user's foot and provides energy to help move user's foot forward between the change in direction of user's foot and foot-strike). Examples of energy storage device 115 includes batteries, capacitors, super capacitors, and other electrical storage devices, hydraulic storage tanks and other pressurized fluid storage devices, pneumatic storage tanks and other compressed air storage devices, and elastic storage devices capable of storing energy over multiple cycles. In some embodiments, energy storage device 115 receives energy from an external source (e.g., battery, power grid, etc.), either intermittently (e.g., charging energy storage device 115 prior to a hike), or continuously. The external source can be body-mounted or carried by the user or remotely mounted (e.g., to a vehicle or building). In some embodiments, an external device is coupled to energy storage device 115 to receive energy therefrom. For example, external device may be a battery (e.g., a standard rechargeable battery used as a power source for another device like a cell phone, computer, light, etc.) or may be a device that directly uses the power supplied by the energy storage device 115 (e.g., a cooling fan powered by a pneumatic energy storage device).

Assist device 120 is coupled to frame 105 and coupled to energy storage device 115 to receive energy therefrom. Assist device 120 is coupled to both frame components 125 and 130 and is configured to produce relative movement between frame components 125 and 130 to assist with movement of user's leg 135. Stored harvested energy from energy storage device 115 powers assist device 120. Assist device 120 assists with movement of user's leg 135 during a portion of a stride of user's leg 135. The assisted portion of the stride may be the same, overlapping, or disjoint (e.g., does not overlap) with the portion of the stride during which energy is harvested. By storing energy over multiple strides, harvested energy may be stored when locomotion is "easy" (e.g., flat terrain) and then used to assist with locomotion when locomotion is "hard" (e.g., uphill terrain). In some embodiments, assist device 120 assists between foot-strike and foot-off. In some embodiments, assist device 120 assists between the change in direction of user's foot from backwards to forwards and foot-strike. Examples of assist device 120 include linear actuators (e.g. ball screws, pistons, etc) and rotary actuators (e.g., motors) and combinations of the two (e.g., a ball screw driven by a motor). In some embodiments, assist device 120 is a brushless DC motor in combination with a ball screw. In some embodiments, the same device may operated as both an energy harvesting device and an assist device (e.g., an electric generator that also acts as a motor, a pneumatic piston that can either act as an air pump or exert force, etc.).

Energy harvesting device 110, energy storage device 115, and assist device 120 can be various combinations of electric devices, hydraulic devices, pneumatic devices, mechanical devices, and electro-mechanical devices. In some embodiments, energy storage device 115 is a compact high-pressure pneumatic composite storage tank, energy harvest device 110 is a pneumatic cylinder, assist device 120 is a pneumatic cylinder, with all three coupled together by small pneumatic tubes.

In some embodiments, leg locomotion device 100 also includes an electronic control unit 140. The electronic control unit or processing circuit 140 can include a processor and memory device. Processor can be implemented as a general purpose processor, an application specific integrated circuit (ASIC), one or more field programmable gate arrays (FPGAs), a group of processing components, or other suitable electronic processing components. Memory device (e.g., memory, memory unit, storage device, etc.) is one or more devices (e.g., RAM, ROM, Flash memory, hard disk storage, etc.) for storing data and/or computer code for completing or facilitating the various processes, layers and modules described in the present application. Memory device may be or include volatile memory or non-volatile memory. Memory device may include database components, object code components, script components, or any other type of information structure for supporting the various activities and information structures described in the present application. According to an exemplary embodiment, memory device is communicably connected to processor via processing circuit and includes computer code for executing (e.g., by processing circuit and/or processor) one or more processes described herein.

Electronic control unit 140 is configured to control various components of leg locomotion device 100, including energy harvesting device 110, energy storage device 115, and assist device 120. Electronic control unit 140 selectively activates energy harvesting device 110 as needed so that energy harvest device 110 is activated and in a harvest mode in which energy is harvested (e.g., at varying levels between a minimum and a maximum level) or deactivated and in an off mode in which energy is not harvested. Similarly, electronic control unit 140 selectively activates assist device 120 as needed so that assist device 120 is activated and in an assist mode in which assist device 120 assists with movement of user's leg 135 (e.g., at varying levels between a minimum and a maximum level) or deactivated and in an off mode in which assistance is not provided to user's leg 135. A manual input provided by the user to electronic control unit 140 or automatic control by electronic control unit 140 can be used to activate and deactivate energy harvesting device 110.

In some embodiments, a harvesting user input device 145 is coupled to electronic control unit 140 and provides the manual input to electronic control unit 140 activate or deactivate energy harvesting device 110. Harvesting user input device 145 allows user to select harvest mode as desired and off mode as desired. Harvesting user input device 145 may also allow the user to vary the level of harvesting (e.g., between a minimum and a maximum level) in harvest mode. In some embodiments, harvesting user input device 145 also allows user to select an automatic position in which electronic control unit 140 automatically controls (i.e., activates, varies, and deactivates) energy harvesting device 110 as needed. Examples of harvesting user input device 145 include switches, dials, touchscreens, buttons, and other manual input devices. In some embodiments, harvesting user input device 145 is a component of a device held, carried, or worn by the user for easy access during locomotion (e.g., a shoe or boot, a remote control, a watch, a hand-held device, a personal music player, a smart-phone, a headband, a hat, a helmet, a belt, a handgrip, a backpack, etc.).

In some embodiments, an assist user input device 150 is coupled to electronic control unit 140 and provides the manual input to electronic control unit 140 activate or deactivate assist device 120. Assist user input device 150 allows user to select assist mode as desired and off mode as desired. Assist user input device 150 may also allow the user to vary the level of harvesting (e.g., between a minimum and a maximum level) in assist mode. In some embodiments, assist user input device 150 actuator also allows user to select an automatic position in which electronic control unit 140 automatically controls (i.e., activates, varies, and deactivates) assist device 120 as needed. Examples of assist user input device 150 include switches, dials, touchscreens, buttons, and other manual input devices.

As shown in FIG. 1, harvesting user input device 145 and assist user input device 150 are coupled to frame component 130. In some embodiments, harvesting user input device 145 and assist user input device 150 are coupled elsewhere on frame 105. In other embodiments, harvesting user input device 145 and assist user input device 150 are included in a remote device (e.g., a remote control, a watch, a personal music player, a smartphone).

Automatic control of energy harvesting device 110 and assist device 120 by electronic control unit 140 can take many forms. Electronic control unit 140 may selectively activate energy harvesting device 110 and/or assist device 120, may control the timing of when to switch between energy harvesting device 110 and assist device 120, may control the amplitude of harvesting and assisting (e.g., harvesting and/or assisting at varying levels between a minimum and a maximum level over a portion of a stride), based on inputs from various sensors (e.g., force, torque, strain, temperature, position, physiological sensors), duration of use of leg locomotion device 100, number of strides made with leg locomotion device 100, level of charge of an energy storage device, etc.

In some embodiments, electronic control unit 140 is configured to automatically control energy harvesting device 110 and assist device 120 in response to a type of terrain upon which user is striding. Types of terrain include uphill, downhill, broken, and flat. In some embodiments, a local terrain sensor 155 detects the type of terrain upon which user is striding. Local terrain sensor 155 is coupled to electronic control unit 140. Examples of local terrain sensors 155 include foot-mounted proximity sensors, simple rangefinders (which sense distance to one or a few points), scanning rangefinders, two-dimensional imaging sensors, and three-dimensional imaging sensors. Any of these may use any suitable means of sensing, for example, laser or optical sensing, microwave sensing, or ultrasonic sensing. Local terrain sensors may provide general terrain parameters such as roughness and slope, or may provide more detailed information, for example the exact height, profile, and likely texture of the surface at the projected location of the next foot strike. A sensor may also include, or be coupled to, a processor which can provide additional information via, e.g., image recognition of terrain features (e.g., rocks, stairs) and surface properties (e.g., soft, hard, slippery, etc.). A sensor may also be able to track a terrain history to indicate terrain slope. For example, a terrain history as determined by an altimeter (e.g., barometric altimeter) can indicate terrain slope. As shown in FIG. 1, local terrain sensor 155 is coupled to frame component 130. In some embodiments, local terrain sensor 155 is coupled elsewhere on frame 105. In other embodiments, local terrain sensor 155 is included in a remote device (e.g., a shoe or boot, a remote control, a watch, a hand-held device, a personal music player, a smart-phone, a headband, a hat, a helmet, a belt, a handgrip, a backpack, etc.).

In other embodiments, a location sensor 160 (e.g., including location determining devices, such as GPS devices) and a terrain information source (e.g. a map) accessible by electronic control unit 140 combine to determine the type of terrain. Location sensor 160 is coupled to electronic control unit 140. Location sensor 160 (e.g., a GPS device) determines the location of user and electronic control unit 140 compares user's location to terrain information source (e.g., from a geographic information system) to determine the type of terrain. As shown in FIG. 1, location sensor 160 is coupled to frame component 130. In some embodiments, location sensor 160 is coupled elsewhere on frame 105. In other embodiments, location sensor 160 is included in a remote device (e.g., a shoe or boot, a remote control, a watch, a hand-held device, a personal music player, a smart-phone, a headband, a hat, a helmet, a belt, a handgrip, a backpack, etc.).

In some embodiments, electronic control unit 140 is configured to automatically control energy harvesting device 110 and assist device 120 in response to a physiological state of user. Physiological states include elevated heart rate or heart rate relative to a threshold, elevated blood pressure or blood pressure relative to a threshold, elevated body temperature or body temperature relative to a threshold, elevated breathing rate or breathing rate relative to a threshold, and elevated blood oxygen level or blood oxygen level relative to a threshold. In some embodiments, a physiological state sensor 165 coupled to user detects the physiological state of user. Physiological state sensor 165 is also coupled to electronic control unit 140. Examples of physiological state sensors 165 include heart rate monitors, blood pressure monitors, body temperature sensors, breathing monitors, sweat sensors, blood oxygen level sensors, electrocardiogram (EKG) sensors, and sensors responsive to muscle motion (e.g., measuring circumference of a limb, measuring strain on a limb, etc.). Physiological state sensor 165 can be directly coupled to user or coupled to user via an item worn by user (e.g., a shoe or boot, a remote control, a watch, a hand-held device, a personal music player, a smart-phone, a headband, a hat, a helmet, a belt, a handgrip, a backpack, etc.). As an example, physiological state sensor 165 allows the electronic control unit 140 to implement a control scheme of maximum energy harvesting at a low heart rate (e.g., near resting heart rate), "neutral" at 80% max heart rate (e.g., no harvesting or assist), and maximum assist at maximum heart rate.

In some embodiments, electronic control unit 140 is configured to automatically control energy harvesting device 110 and assist device 120 in response to a nervous system signal detected by a neuroelectric sensor 170. Neuroelectric sensor 170 is coupled to electronic control unit 140 and coupled to user to detect a nervous system signal generated by the user's nervous system. Neuroelectric sensor 170 can be directly coupled to user or coupled to user via an item worn by user (e.g., a shoe or boot, a remote control, a watch, a hand-held device, a personal music player, a smart-phone, a headband, a hat, a helmet, a belt, a handgrip, a backpack, etc.).

In some embodiments, electronic control unit 140 is configured to automatically control energy harvesting device 110 and assist device 120 in response to a load exerted on frame 105. A frame load sensor 175 is coupled to frame 105 to detect the load exerted on frame 105. Frame load sensor 175 is also coupled to electronic control unit 140. Load exerted on frame 105 can be a force, strain, or torque indicative of user striding across uphill, broken, or other difficult terrain. Examples of frame load sensors 175 include force sensors, strain sensors, and torque sensors. The detected load can be compared to a threshold load such that electronic control unit 140 selectively activates energy harvesting device 110 and assist device 120 based on the comparison. For example, energy harvesting device 110 is activated when detected load is above threshold and deactivated when detected load is below threshold. As another example, assist device 120 is activated when detected load is below threshold and deactivated when detected load is above threshold. Threshold load can be input manually, determined based on a frame load history of user (e.g., to determine when user is "working hard" and needs assistance and/or to determine when user is not "working hard" and can harvest energy), or determined in other appropriate manners.

In some embodiments, electronic control unit 140 is configured to automatically control energy harvesting device 110 and assist device 120 in response to a position of frame 105. A frame position sensor 180 is coupled to frame 105 to detect the position of frame 105. Frame position sensor 180 is also coupled to electronic control unit 140. The detected position of frame 105 can be a relative position between frame components 125 and 130, a relative position between frame position sensor 180 and a constant (e.g., sea level or other elevation) or a relative position between frame position sensor 180 and a calculated level ground position (e.g., position of frame position sensor 180 when user's foot is on level ground). In this way, frame position sensor 180 can be used to detect when actual foot-strike occurs either before or after expected foot-strike with calculated level ground position, thereby indicating when user is striding across uphill, downhill, or broken terrain. Constants and calculated level ground position can be considered a threshold position against which the detected frame position is compared. Threshold position can also be determined based on a frame position history of user. Examples of frame position sensors 180 include encoders, displacement sensors, and rangefinders (e.g. laser, acoustic).

In some embodiments, electronic control unit 140 is configured to automatically control energy harvesting device 110 and assist device 120 in response to a load exerted on user. A user load sensor 185 is coupled to user to detect the load exerted on user. User load sensor 185 is also coupled to electronic control unit 140. Load exerted on user can be a force, strain, or torque indicative of user striding across uphill, broken, or other difficult terrain. Examples of user load sensors 180 include force sensors, strain sensors, and torque sensors. The detected load can be compared to a threshold load such that electronic control unit 140 selectively activates energy harvesting device 110 and assist device 120 based on the comparison. For example, energy harvesting device 110 is activated when the detected load is above the threshold and deactivated when the detected load is below the threshold. As another example, assist device 120 is activated when the detected load is below the threshold and deactivated when the detected load is above the threshold. Threshold load can be input manually, determined based on a user load history of user (e.g., to determine when user is "working hard" and needs assistance and/or to determine when user is not "working hard" and can harvest energy), or determined in other appropriate ways. User load sensor 185 may be included in or a component of a piece of footwear or other item worn by user (e.g., e.g., a shoe or boot, a remote control, a watch, a hand-held device, a personal music player, a smart-phone, a headband, a hat, a helmet, a belt, a handgrip, a backpack, etc.). For example, user load sensor 185 may included in user's shoe and configured to detect the load that occurs at foot-strike.

In some embodiments, electronic control unit 140 is configured to automatically control energy harvesting device 110 and assist device 120 in response to a harvesting history of user and/or an assist history of user. Electronic control unit 140 can be configured to tracking conditions (e.g., terrain, temperature, elevation, location, inputs from various sensors described above) present when energy harvesting device 110 is activated and conditions present when energy harvesting device 110 is deactivated to compile a harvesting history of user. Similarly, an assist history of user can be compiled. Electronic control unit 140 can evaluate these histories, alone or in combination, to optimize harvesting and assistance based on past usage or adapt to user's gait, habits, or other personal characteristics.

Referring to FIG. 2, a leg locomotion system 200 according to an exemplary embodiment is illustrated. Leg locomotion system includes multiple leg locomotion devices 205, 210, 215, and 220 similar to leg locomotion device 100 described above. In some embodiments, fewer leg locomotion devices (as few as two) are included in leg locomotion system 200. Leg location motion device 205 is mounted at user's hip. Leg locomotion device 210 is mounted at user's knee. Leg locomotion device 215 is mounted at user's ankle. Leg location device 220 is mounted at the arch of user's foot.

In some embodiments, leg locomotion devices 205, 210, 215, 220 are distinct from one another. In other embodiments, leg locomotion devices 205, 210, 215, 220 share one or more frame components. In some embodiments, leg locomotion system 200 includes a common energy storage device 225 coupled to and shared by leg locomotion devices 205, 210, 215, 220. This allows energy harvested by one of leg locomotion devices 205, 210, 215, 220 to used for assistance by a different leg locomotion devices 205, 210, 215, 220. Similarly, in some embodiments, a shared electronic control unit 230 is coupled to and shared by leg locomotion devices 205, 210, 215, 220. Shared energy storage device 225 and shared electronic control unit 230 can be mounted on one of leg locomotion devices 205, 210, 215, 220 or mounted remotely (e.g., a shoe or boot, a remote control, a watch, a hand-held device, a personal music player, a smart-phone, a headband, a hat, a helmet, a belt, a handgrip, a backpack, etc.).

In some embodiments, leg locomotion system 200 includes at least one leg locomotion device mounted on user's right leg and at least one leg locomotion device mounted on user's left leg. Shared energy storage device 225 and shared electronic control unit 230 can be shared amongst leg locomotion devices mounted on both legs.

Figure 3:
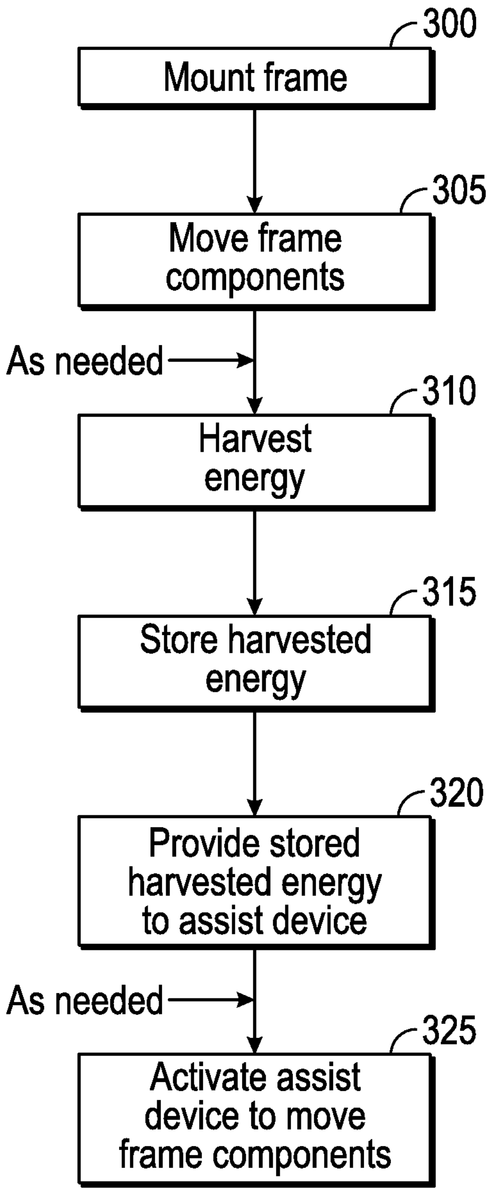
FIG. 3 is a flowchart of a method of operating leg locomotion device of FIG. 1 according to an exemplary embodiment.

Referring to FIG. 3, in a method according to an exemplary embodiment, leg locomotion device 100 is operated. Frame 105 is mounted user's leg 135 (step 300). Frame 105 can mounted at user's hip, knee, ankle, or arch of foot. Frame components 125 and 130 are moved relative to one another in response to movement of user's leg 135 (step 305). Energy is harvested from movement of two frame components 125 and 130 during a portion of a stride of user's leg 135 with energy harvesting device 110 (step 310). Energy can be harvested in any appropriate form (e.g., mechanical, pneumatic, hydraulic, electric, etc.). Energy harvesting can be selectively activated as needed, as described above with respect to leg locomotion device 100. Harvested energy is stored in energy storage device 115 over more than one stride of user's leg 135 (step 315). Energy can be stored as one of pneumatic, hydraulic, and electric energy. Energy from energy storage device 135 is provided to assist device 120 (step 320). Energy can be provided as one of pneumatic, hydraulic, and electric energy. Assist device 120 is activated to move frame components 125 and 130 with respect to one another to assist with movement of user's leg 135 during a portion of the stride of user's leg 135 (step 325). Assistance can be selectively activated as needed, as described above with respect to leg locomotion device 100.

Figure 4:
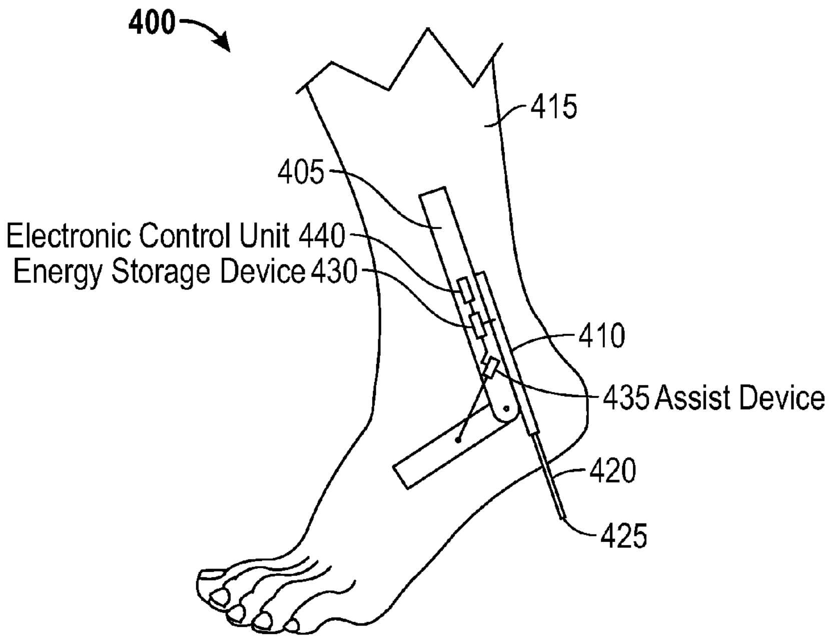
FIG. 4 is a schematic diagram of a leg braking device according to an exemplary embodiment.

Referring to FIG. 4, a leg braking device 400 is illustrated according to an exemplary embodiment. Striding is more efficient going uphill or upslope than downhill or downslope. When striding downhill, a person expends energy to keep himself upright (i.e., not fall down) counter to gravity, which is working to propel person downhill. Leg braking device 400 is configured to reduce the energy expenditure of person striding downhill by braking user's downhill stride through the absorption of energy. In some embodiments, leg braking device 400 is combined with the components of leg locomotion device 100 described above to result in a leg locomotion device with leg braking functionality included.

Leg braking device 400 includes a frame 405 and an energy absorbing device 410. Frame 405 is mounted to user's leg 415. Energy absorbing device 410 is coupled to frame 405 and absorbs a downhill load associated with a downhill stride. For example, energy absorbing device 410 absorbs the load due to the change in elevation from foot-off to foot-strike of a downhill stride of the user's leg 415.

In some embodiments, leg braking device 400 is body-fitting, that is neither frame 405 nor energy absorbing device 410 extends beyond the bottom of user's foot.

In some embodiments, energy absorbing device 410 includes one or more extensions 420. Extensions 420 extends past the sole of a user's foot. The extensions 420 may be integrated into the user's shoe or boot (e.g., the extension 420 is a portion of the sole that pivots or moves relative to the rest of the shoe or boot). Extension 420 terminates at a ground-engaging end 425. Extension 420 is movable between an extended position in which surface-engaging end 425 extends beyond the bottom of user's foot and a retracted position in which surface-engaging end 425 does not extend beyond the bottom of the user's foot. The extended position may be a fixed length past the sole or extend for a variable length past the sole that may be user controlled or automatically controlled. For example, the length of the extended position may vary in response to changes in the slope of the terrain being traversed or in response to the type of terrain being traversed (e.g., smooth or rocky). The length of the extended position may also vary in response to the amount of desired energy harvesting (e.g., a longer length to harvest more energy). Movement of extension 420 from the extended position and the retracted position causes energy absorbing device 410 to absorb at least a portion of the associated load. In some embodiments, extension 420 is a component of a shock absorber acting as energy absorbing device 410.

In some embodiments, an energy storage device 430 is coupled to energy absorbing device 410, which is configured to convert at least a portion of the absorbed downhill load to energy. Energy storage device 430 stores the converted energy over more than one stride of user's leg 415. In some embodiments, the entirety of the absorbed downhill load is converted to energy. In some embodiments, energy storage device 430 is similar to energy storage device 115 described above.

In some embodiments, an assist device 435 is coupled to energy storage device 430 to receive energy therefrom. Assist device 435 is similar to assist device 120 described above and is configured to move frame 405 (e.g. two frame components) to assist with movement of user's leg 415 during a portion of a stride of user's leg 415.

In some embodiments, an external device is coupled to energy storage device 430 to receive energy therefrom. For example, external device may be a battery (e.g., a standard rechargeable battery used as a power source for another device like a cell phone, computer, light, etc.) or may be a device that directly uses the power supplied by the energy storage device 430 (e.g., a cooling fan powered by a pneumatic energy storage device).

In some embodiments, an electronic control unit 440 (similar to electronic control unit 140 described above) is coupled to energy absorbing device 410, energy storage device 430, and assist device 435 to control (e.g., automatically or via manual input) these devices as explained above with respect to leg locomotion device 100 (e.g., in response to sensors of various types including force, torque, strain, temperature, position, and physiological sensors). Sensors associated with the downhill leg braking device 400 may further include extension sensors associated with the one or more extensions 420 (e.g., a surface engaging end-to-surface range sensor, velocity sensors (axial and transverse), proximity sensors, a contact sensor for detecting contact by the surface-engaging end 425, axial and transverse (bending) force sensors, and sensors to detect the length and or velocity of the extensions 420). Any multi-directional or multi-axial sensors or combination of sensors may be used to detect twisting or other multi-directional movement of the leg braking device 400 that may be indicative of unwanted twisting or slipping (e.g., on a rock or uneven terrain) and may deactivate a planned harvesting cycle to avoid tripping or otherwise impeding the movement of the user under these conditions.

Figure 5:
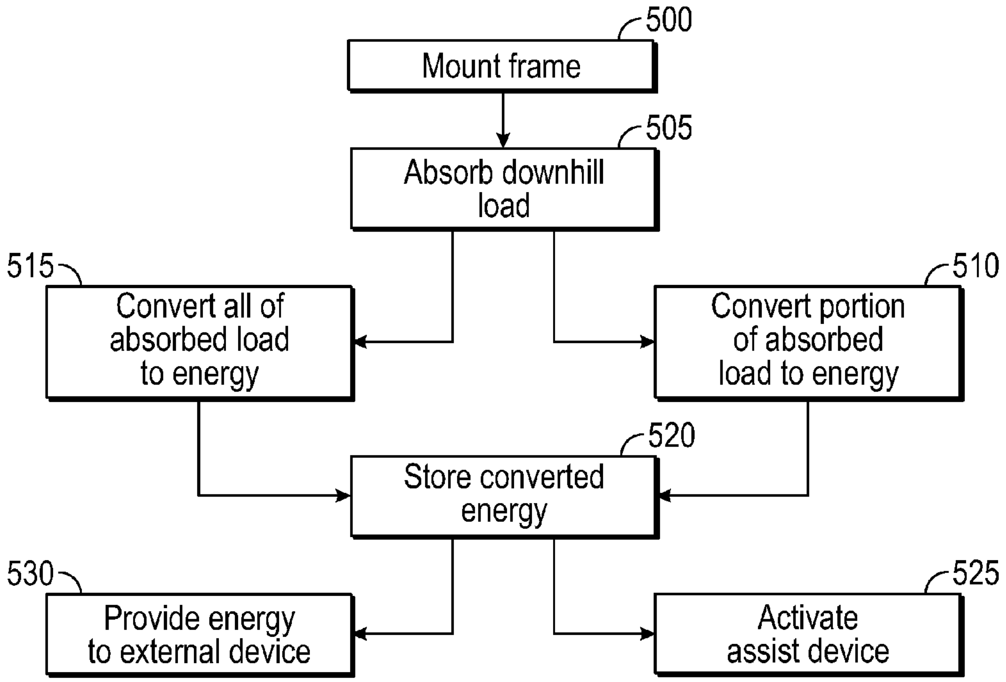
FIG. 5 is a flow chart of a method of braking a leg during downhill striding using the leg braking device of FIG. 4 according to an exemplary embodiment.

Referring to FIG. 5, a method of braking during downhill striding is illustrated according to an exemplary embodiment. First, frame 405 is mounted to user's leg 415 (step 500). Energy absorbing device 410 absorbs a downhill load associated with a change in elevation from foot-off to foot-strike of a downhill stride of user's leg 415, thereby braking the user's progress downhill (step 505). In some embodiments, step 505 includes moving extension 420 from the extended position to the retracted position. In some embodiments, at least a portion of the absorbed downhill load is converted to energy (step 510). In other embodiments, all of the absorbed downhill load is converted to energy (step 515). Converted energy is stored in energy storage device 430 for more than one stride of user's leg 415 (step 520). In some embodiments, stored converted energy is provided to assist device 435, which is activated as needed to move frame 405 to assist with movement of user's leg 415 during a portion of a stride of user's leg 415 (step 525). In some embodiments, stored converted energy is provided to an external device (step 530).

The construction and arrangement of the apparatus, systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, some elements shown as integrally formed may be constructed from multiple parts or elements, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show or the description may provide a specific order of method steps, the order of the steps may differ from what is depicted. Also two or more steps may be performed concurrently or with partial concurrence. Such variation will depend on various factors, including software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A leg locomotion device, comprising:

a frame having a leg coupler configured to mount the frame to a user's leg, the frame also including two frame components movable with respect to one another in response to movement of the user's leg;

an energy harvesting device coupled to the frame and configured to harvest energy from the movement of the two frame components during a first portion of a stride;

an energy storage device coupled to the energy harvesting device, the energy storage device configured to store harvested energy over more than one stride of the user's leg;

an assist device coupled to the frame, coupled to the energy storage device to receive energy therefrom, and configured to produce relative movement between the frame components to selectively assist with movement of the user's leg during a second portion of the stride;

an electronic control unit configured to selectively and automatically actuate the assist device to control movement of the assist device to use the energy harvested over more than one stride of the user's leg to produce the relative movement between the two frame components;

a location sensor coupled to the electronic control unit and configured to detect a location of the user; and a terrain information source accessible by the electronic control unit;

wherein the electronic control unit is further configured to compare the detected location of the user to the terrain information source to determine the type of terrain upon which the user is striding.

2. The leg locomotion device of claim 1, wherein the electronic control unit is configured to automatically control the energy harvesting device to control when the energy harvesting device harvests energy and configured to automatically control the assist device to control when the assist device assists movement of the user's leg.

3. The leg location device of claim 2, wherein the electronic control unit is configured to control at least one of the energy harvesting device and the assist device in response to a manual input provided by the user.

4. The leg locomotion device of claim 3, further comprising:

a harvesting user input device coupled to the electronic control unit and configured to provide the manual input to control the energy harvesting device.

5. The leg locomotion device of claim 4, further comprising:

an assist user input device coupled to the electronic control unit and configured to provide the manual input to control the assist device.

6. The leg locomotion device of claim 3, further comprising:

an assist user input device coupled to the electronic control unit and configured to provide the manual input to control the assist device.

7. The leg locomotion device of claim 2, wherein the electronic control unit is configured to automatically control a level at which the energy harvesting device harvests energy and configured to automatically control a level at which the assist device assists movement of the user's leg.

8. The leg locomotion device of claim 2, wherein the electronic control unit is configured to automatically control the energy harvesting device and to automatically control the assist device in response to a type of terrain upon which the user is striding.

9. The leg locomotion device of claim 8, further comprising:

a local terrain sensor coupled to the electronic control unit and configured to detect the type of terrain upon which the user is striding.

10. The leg locomotion device of claim 7, wherein the electronic control unit is configured to automatically control the energy harvesting device and to automatically control the assist device in response to a physiological state of the user.

11. The leg locomotion device of claim 10, further comprising:

a physiological state sensor coupled to the electronic control unit and configured to be coupled to the user to detect the physiological state of the user.

12. The leg locomotion device of claim 7, wherein the electronic control unit is configured to automatically control the energy harvesting device and to automatically control the assist device in response to a load exerted on the frame.

13. The leg locomotion device of claim 12, further comprising:

a frame load sensor coupled to the frame, coupled to the electronic control unit, and configured to detect the load exerted on the frame;

wherein the electronic control unit is configured to automatically control the energy harvesting device based on a comparison between the detected load and a threshold load.

14. The leg locomotion device of claim 13, wherein the electronic control unit is configured to automatically control the assist device based on a comparison between the detected load and a threshold load.

15. The leg locomotion device of claim 7, wherein the electronic control unit is configured to automatically control the energy harvesting device and to automatically control the assist device in response to a position of the frame.

16. The leg locomotion device of claim 15, further comprising:

a frame position sensor coupled to the frame, coupled to the electronic control unit, and configured to detect the position of the frame;

wherein the electronic control unit is configured to automatically control the energy harvesting device based on a comparison between the detected position and a threshold position.

17. The leg locomotion device of claim 16, wherein the electronic control unit is configured to automatically control the assist device based on a comparison between the detected position and a threshold position.

18. The leg locomotion device of claim 7, wherein the electronic control unit is configured to automatically control the energy harvesting device and to automatically control the assist device in response to a load exerted on the user.

19. The leg locomotion device of claim 18, further comprising:

a user load sensor coupled to the user, coupled to the electronic control unit, and configured to detect the load exerted on the user;

wherein the electronic control unit is configured to automatically control the energy harvesting device based on a comparison between the detected load and a threshold load.

20. The leg locomotion device of claim 19, wherein the electronic control unit is configured to selectively activate the assist device based on a comparison between the detected load and a threshold load.

21. The leg locomotion device of claim 7, wherein the electronic control unit is configured to automatically control the energy harvesting device in response to a harvesting history of the user and an assist history of the user and to automatically control the assist device in response to the harvesting history of the user and the assist history of the user.

22. The leg locomotion device of claim 1, wherein the frame is configured to be mounted at the user's hip.

23. The leg locomotion device of claim 1, wherein the frame is configured to be mounted at the user's knee.

24. The leg locomotion device of claim 1, wherein the frame is configured to be mounted at the user's ankle.

25. The leg locomotion device of claim 1, wherein the frame is configured to be mounted at the arch of the user's foot.

26. The leg locomotion device of claim 1, wherein the energy harvesting device is one of a piston, a generator, a pump, and a compressor.

27. The leg locomotion device of claim 1, wherein the energy storage device is one of an accumulator, a battery, a capacitor, a pneumatic storage tank, a hydraulic fluid storage tank, and an elastic storage device.

28. The leg locomotion device of claim 1, wherein the assist device is one of a rotary actuator, a linear actuator, a piston, and a ball screw.

29. The leg locomotion device of claim 1, wherein the first portion of the stride and the second portion of the stride are a same portion of the stride.

30. The leg locomotion device of claim 1, wherein the first portion of the stride overlaps the second portion of the stride.

31. The leg locomotion device of claim 1, wherein the first portion of the stride does not overlap the second portion of the stride.

32. A leg locomotion system, comprising:

a first leg locomotion device, including, a first frame configured to be mounted to a user's leg proximate a first leg joint, the first frame including two first frame components movable relative to one another in response to movement of the user's leg at the first leg joint, a first energy harvesting device coupled to the first frame and configured to harvest energy from the movement of the two first frame components during a portion of a stride of the user's leg, and a first assist device coupled to the first frame and configured to move the first frame components relative to one another to selectively assist with movement of the user's leg at the first leg joint during a portion of the stride;

a second leg locomotion device, including, a second frame configured to be mounted to the user's leg proximate a second leg joint, the second frame including two second frame components movable relative to one another in response to movement of the user's leg at the second leg joint, a second energy harvesting device coupled to the second frame and configured to harvest energy from the movement of the two second frame components during a portion of the stride, and a second assist device coupled to the second frame and configured to move the second frame components relative to one another to selectively assist with movement of the user's leg at the second leg joint during a portion of the stride;

an energy storage device coupled to the first and second energy harvesting devices, the energy storage device configured to store harvested energy from the first and second energy harvesting devices over more than one stride, and the energy storage device coupled to the first and second assist devices to provide energy thereto;

an electronic control unit configured to selectively and automatically actuate the first and second assist devices to control when each of the first and second assist devices assists movement of the user's leg;

a location sensor coupled to the electronic control unit and configured to detect a location of the user; and a terrain information source accessible by the electronic control unit;

wherein the electronic control unit is further configured to compare the detected location of the user to the terrain information source to determine the type of terrain upon which the user is striding;

wherein at least one of the first assist device and the second assist device includes a pneumatic device.

33. The leg locomotion system of claim 32, wherein the electronic control unit is further configured to automatically control the first and second energy harvesting devices to control when each of the first and second energy harvesting devices harvests energy.

34. A method of operating a leg locomotion device, comprising:

mounting a frame to a user's leg, the frame including two frame components movable relative to one another;

moving the two frame components in response to movement of the user's leg;

harvesting energy from the movement of the two frame components during a first portion of a stride of the user's leg with an energy harvesting device;

storing harvested energy in an energy storage device over more than one stride of the user's leg;

providing energy from the energy storage device to an assist device; and activating the assist device to move the two frame components relative to one another to assist with movement of the user's leg during a second portion of the stride;

detecting, by a location sensor, a location of the user; and comparing, by an electronic control unit, the detected location of the user to a terrain information source to determine a type of terrain upon which the user is striding;

wherein the electronic control unit selectively and automatically actuates the assist device to use the energy harvested over more than one stride of the user's leg to assist with movement of the user's leg during the second portion of the stride.

* * * * *